United States Patent [19]

Carr et al.

[11] Patent Number: 4,642,396
[45] Date of Patent: Feb. 10, 1987

[54] PROCESS FOR SEPARATING NITROAROMATIC COMPOUNDS FROM SPENT NITRIC ACID

[75] Inventors: Richard V. C. Carr; Bernard A. Toseland, both of Allentown, Pa.; David S. Ross, Palo Alto, Calif.

[73] Assignee: Air Products and Chemicals, Inc., Allentown, Pa.

[21] Appl. No.: 638,436

[22] Filed: Aug. 7, 1984

[51] Int. Cl.$^4$ .................. C07C 79/10; C07B 43/02
[52] U.S. Cl. .................. 568/934; 260/688
[58] Field of Search ............ 260/688; 568/927, 932, 568/934

[56] References Cited

U.S. PATENT DOCUMENTS

| | | | |
|---|---|---|---|
| 1,325,168 | 12/1919 | Perruche . | |
| 2,362,743 | 11/1944 | Crater | 260/645 |
| 2,656,395 | 10/1953 | Benson | 568/927 |
| 2,736,742 | 2/1956 | Gyttorp | 260/467 |
| 2,739,174 | 3/1956 | Ross | 260/645 |
| 2,849,497 | 8/1958 | Buchanan | 260/645 |
| 2,867,669 | 1/1959 | Burkhard | 568/927 |
| 2,883,432 | 4/1959 | Spaeth | 568/927 |
| 3,185,738 | 5/1965 | Cossaboon et al. | 260/645 |
| 3,204,000 | 12/1961 | Samuelsen | 568/934 |
| 3,780,116 | 12/1973 | Sahgal | 260/645 |
| 3,975,452 | 8/1976 | Mayer et al. | 568/934 |
| 4,028,425 | 6/1977 | Gilbert | 568/934 |
| 4,112,005 | 9/1978 | Thiem et al. | 260/645 |
| 4,123,466 | 10/1978 | Lin et al. | 260/645 |
| 4,257,986 | 3/1981 | Milligan et al. | 568/934 |
| 4,261,908 | 4/1981 | Schroeder et al. | 260/369 |
| 4,496,782 | 1/1985 | Carr | 568/934 |
| 4,517,394 | 5/1985 | Wang et al. | 568/947 |

FOREIGN PATENT DOCUMENTS

964183  7/1964  United Kingdom ............ 568/934

*Primary Examiner*—John F. Terapane
*Assistant Examiner*—Eric Jorgensen
*Attorney, Agent, or Firm*—Russell L. Brewer; E. Eugene Innis; James C. Simmons

[57] ABSTRACT

This invention pertains to a process for extracting a nitroaromatic composition from a nitration medium containing nitric acid, water, and nitroaromatic. The process comprises contacting the nitration medium with nitric oxide under conditions such that the nitric oxide will react with the nitric acid to form nitrogen dioxide and water. Gaseous nitrogen dioxide is removed from the reaction medium and accordingly, the dissolved nitroaromatic present in the nitration medium separates to form an organic phase which then can be removed by decantation. Typically, one mole of nitric oxide is added to the nitration medium for every two moles of nitric acid present in said medium. Reaction conditions normally are from about 0° to 90° C.

8 Claims, No Drawings

PROCESS FOR SEPARATING NITROAROMATIC COMPOUNDS FROM SPENT NITRIC ACID

TECHNICAL FIELD

This invention relates to a process for efficient separation of nitroaromatic compositions from a reaction product comprising nitric acid, unreacted aromatic compound and nitroaromatic.

BACKGROUND OF THE INVENTION

Nitroaromatic compositions have been widely used as intermediates in the chemical industry, and are well suited for producing a variety of industrial chemicals such as aromatic amines for use as chain extenders in polyurethane manufacture or in preparation of aromatic isocyanates for urethane synthesis. Examples of widely used nitroaromatic compositions include mono and dinitrobenzene, mono and dinitrotoluene and mono and dinitroxylene.

Numerous processes have been developed for effecting nitration of aromatic hydrocarbons. The conventional procedure for nitrating hydrocarbons has been the mixed acid process wherein concentrated nitric acid and concentrated sulfuric acid are used as the nitrating medium. This process is referred to as the mixed acid process and has been preferred over other nitration procedures since nitration can proceed at a more effective rate due to increased nitronium ion concentration in the nitration medium. Subsequent to nitration, the nitroaromatic is separated from the spent acid phase and further nitration effected, if desired, by recycling the mono or dinitrated aromatic to a subsequent nitration zone. Representative patents which disclose mixed acid techniques include U.S. Pat. Nos. 2,849,497; 3,185,738; and 4,123,466. The U.S. Pat. No. 4,123,466 differs from the other two patents in that nitrogen dioxide is injected into the reaction medium of aromatic compound and sulfuric acid as opposed to nitric acid injection into the reaction medium.

Numerous processes have also been developed which utilize nitric acid alone as the nitrating agent in the manufacture of both mono and dinitroaromatic compounds. Typically, when the dinitro compound is prepared, a more concentrated nitric acid is utilized, e.g. fuming nitric acid as the nitrating agent than when the mononitroaromatic is prepared. Representative patents which disclose various nitration processes using nitric acid along include U.S. Pat. Nos. 2,362,743; 2,739,174; 3,780,116; and 4,112,005. Although the processes employ nitric acid as the nitration medium, they differ in the selectivity to either mono or dinitrated product produced or in the use of different mole ratios of nitric acid to aromatic compounds or in the use of different process techniques to effect nitration.

Another form of nitration procedure for producing nitrated aromatic composition resides in the use of nitrogen oxides alone or in combination with sulfuric acid or oxygen as the nitrating medium. Various nitrogen oxides such as $N_2O_5$, $NO_2$ and $N_2O_4$ have been utilized as the nitrating agent. The U.S. Pat. No. 4,028,425 provides for the introduction of nitrogen dioxide and oxygen into an aromatic hydrocarbon with the coproduction of the dinitroaromatic compound and concentrated nitric acid as a product.

Each of the processes described above requires separation of the nitroaromatic compound from the unreacted aromatic compound and spent nitric acid. Typically, the spent nitric acid contains a substantial amount of water which must be removed in order to recover the spent nitric acid and recovering the unreacted aromatic hydrocarbon. Recovery of residual nitric acid in the reaction product is a major commercial object in preparing dinitroaromatic compounds where the amount of residual acid is substantial. In mononitration reactions the amount of residual nitric acid may be less than in dinitration reactions, and recovery may not be as important as is the separation of the nitroaromatic and unreacted aromatic compounds from the spent acid.

Various techniques have been developed to recover nitric acid from the spent acid in a nitration process. For example, U.S. Pat. No. 4,257,986 discloses the separation of the organic phase from the spent acid phase in a mixed acid nitration process and then introducing unreacted aromatic compound into the spent acid phase under nitrating conditions to generate mononitroaromatic compound. The reaction product then is allowed to separate into various phases and the aqueous phase removed from the organic phase containing the nitroaromatic compound and unreacted aromatic.

U.S. Pat. No. 2,849,497 discloses the separation of the organic layer from the aqueous layer which consists primarily of nitric acid, sulfuric acid, nitroaromatic compound and water. The U.S. Pat. No. 2,849,497 process involves the introduction of additional unreacted aromatic compounds into the spent acid phase to denitrate the spent acid. The advantage of the process is that the nitric acid, which is dissolved in the crude nitroaromatic, is advantageously recovered for the preparation of additional product rather than being washed out first.

One of the more conventional techniques for removing spent nitric acid from the reaction mixture, with either the mixed acid process, the nitric acid process or a nitrogen oxides process, is the neutralization of the spent acid by reaction with alkali and the products thus separated. For example, U.S. Pat. No. 1,325,168 discloses the neutralization of the nitric acid with a base, such as lime, ammonia, or the like, and then removing the nitrobenzene in a pure state by distillation. Solvent extraction using carbon tetrachloride is also suggested as being an alternative to the neutralization technique.

U.S. Pat. No. 2,736,742 discloses the uses of a mixture or solution of ammonia and organic bases with ammonia nitrate to effect removal of nitric acid.

U.S. Pat. No. 4,261,908 discloses the separation of dinitroaromatics from nitric acid by distillation.

The separation of nitric acid from nitroaromatic compositions produced in aromatic dinitration processes has been a continuing problem. The problem is more severe in dinitration reactions than in mononitration reactions and is more severe in those processes using nitric acid alone as the nitrating medium. Several reasons are apparent. First, the spent nitric acid present in a dinitration reaction has a much higher concentration than normally used when a mixed acid process is used. Second, removal of the nitric acid typically cannot be effected by the introduction of fresh aromatic because such conditions are not suited for nitration. On the other hand, modest nitration can be achieved by the mixed acid process to the mononitro product. Thirdly, the processes which rely on neutralization techniques in an effort to recover nitrated aromatic compounds from the nitration wash liquors as represented in the U.S. Pat. No. 4,241,229 disclose problems with respect to the sewering and problems associated with biological treatment.

SUMMARY OF THE INVENTION

This invention pertains to a process for extracting nitroaromatic compositions from a nitric acid medium generated in the nitration of aromatic compounds. The reaction product typically contains nitroaromatic compound, nitric acid, and water. Optionally unreacted aromatic and miscellaneous byproducts may be present in the nitration product medium. The extraction process is achieved by introducing nitric oxide (NO) into the nitric acid medium under conditions sufficient to react with the nitric acid present therein to generate nitrogen dioxide ($NO_2$) and water. The gaseous nitrogen dioxide then can be removed from the nitration medium and subsequently used to regenerate or form nitric acid.

The major advantages of the process of this invention are:

- it permits recovery of nitric acid from a nitration medium containing dissolved nitroaromatic at low temperature, thus avoiding hazardous distillation conditions associated with the separation of dinitrotoluene;
- it permits the recovery of the nitric acid in a form which can be regenerated to form a reactant for the nitration process; and
- it permits efficient recovery of the nitroaromatic from a spent acid phase at low temperature, thereby reducing product loss due to dissolved nitroaromatic in the acid phase.

DETAILED DESCRIPTION OF THE INVENTION

The process of this invention can be utilized for the recovery of nitric acid from the nitration of aromatic compounds using nitric acid along, the mixed acid technique or a mixture of nitrogen oxides wherein the reaction product contains nitroaromatic dissolved in nitric acid and water. Typical aromatics formed by these nitration processes include nitrobenzene, nitrotoluene and nitroxylene.

The recovery of nitric acid from the nitration medium is achieved by introducing nitric oxide into the reaction medium under conditions sufficient for the nitric oxide to react with the nitric acid to form gaseous nitrogen dioxide and water. Sufficient nitric oxide must be added to the nitration medium in order to react with the residual nitric acid in the medium to generate the product nitrogen dioxide and water. As the concentration of nitric acid in the spent acid phase is reduced, nitroaromatic compounds will be forced from the spent acid or aqueous phase and into the organic phase. The nitrogen dioxide generated by the reaction between nitric oxide and nitric acid is removed as a gas and can be further oxidized in a separate unit to form nitric acid for further reaction. The water which is formed in the reaction between nitric acid and nitric oxide is a byproduct and can simply be disposed of through a conventional waste treatment system.

Conditions suited for the reaction of nitric oxide with nitric acid to gaseous nitrogen oxides are typically from about 0° to 90° C. Temperatures lower than about 70° C. achieve the recovery of nitric acid from the nitration medium while simultaneously effecting extraction of the nitroaromatic from the nitration medium.

In order to recover substantially all of the nitric acid in the spent acid phase, sufficient nitric oxide must be introduced into the unit to achieve sufficient reduction or the nitric acid to generate an insoluble organic fraction. Normally at least one mole of nitric oxide is required to react with two moles of nitric acid in order to effect full decomposition of the nitric acid. For purposes of practicing the invention, it is preferred that a slight excess, e.g. 10% greater than stoichiometric amounts are used in order to insure that substantially all of the nitric acid is recovered. The excess nitric oxide can then be oxidized to nitrogen dioxide for subsequent conversion to nitric acid. Therefore, there is little, if any, loss of the nitric acid or nitric oxide in the extraction of the nitroaromatic from the spent acid phase and effect recovery of the nitric acid.

The following examples are provided to illustrated various embodiments of the invention and are not intended to restrict the scope thereof.

EXAMPLE 1

Decomposition of Nitric Acid by NO to Extract 2,4-Dinitrotoluene

In this run 2,4-dinitrotoluene was added to aqueous nitric acid to demonstrate the NO decomposition of nitric acid in a simulated nitration medium environment.

To a reaction flask was added 15.09 g (215 mm) of aqueous 90% nitric acid and 1.023 g of 2,4-dinitrotoluene. The reaction mixture was maintained at 70° C., while NO and $N_2$ were being bubbled through the mixture. The gases were introduced at a rate of 13 standard cubic centimeters per minute (sccm) and approximately 50 sccm, respectively. Nitrogen was added as a diluent to aid agitation of the mixture. The reaction was carried out for 188 minutes, during which time 114.2 mmole of NO were passed. The weight of the material remaining in the reactor was 7.49 g of which 1.001 g were recovered as 2,4-dinitrotoluene. Thus, 97.9% of 2,4-dinitrotoluene of the original 2,4-dinitrotoluene was recovered. The remaining 6.49 g of material was determined to be aqueous nitric acid with strength of 52.6% by weight, this represents 54.13 mmole $HNO_3$ and 171.11 mmole $H_2O$. The amount of $H_2O$ formed equal 87.2 mmole and the amount of $HNO_3$ decomposed was by difference 161.43 mmole. These results show the efficiency of nitric acid decomposition by NO in this experiment was approximately 71%.

The above experiment demonstrates NO decomposition as an extraction technique for separating. In the case described one can work at or near the melting point of the material to be extracted to keep it in the liquid phase as its concentration increases and as the acid is decomposed. Then, by reducing the temperature the solid material can be either filtered off and washed, or solvent extracted from the remaining acid. For example, separation can be effected by cooling the reaction medium to solidify the dinitroaromatic and then the solidified nitroaromatic removed from the medium by filtration, etc., or alternatively allowing the dinitrotoluene to separate into an organic layer and the water in an aqueous layer and then decanting the organic layer from the aqueous layer.

EXAMPLE 2

Decomposition of Nitric Acid by NO to Extract 2,4-Dinitrotoluene

To a reaction flask was added 10 ml of 90% $HNO_3$ (13.35 g or 211.90 mmole $HNO_3$) and 1.48 g or 82.22 mmole $H_2O$ along with 1.167 g (6.41 mmole) 2,4-dinitrotoluene to simulate 15.99 g of nitration medium obtained from the dinitration of toluene. NO and $N_2$ were passed through this mixture at 26 sccm and 50 sccm, respectively. Total reaction time was 98 minutes with 114.33 mmole of NO being passed. A dry ice-carbon tetrachloride trap maintained at $-23°$ C. was used to condense the material driven from the nitration medium.

The reaction generated, as in Example 1, copious amounts of brown fumes in the head-space above the reaction liquid, which were identified as $NO_2$. The material trapped overhead weighed 11.37 g which represents 71.1% of the starting material on a weight basis. To make sure that the light flow of $N_2$ used during the reaction was not entraining water or nitric acid was following was done. The trap was raised to room temperature and $N_2$ at 1 sccm was passed through the trap. After a period of venting condensed gases, which vaporized at the low elevated temperature, 0.648 g of liquid was left. This liquid was assumed to be any entrained water or nitric acid, this represents 4.1% of the starting material. A gc analysis showed the trapped material to be free of any 2,4-dinitrotoluene.

The material remaining in the reactor weighed 5.92 g. Upon separation, 1.145 g of the starting 2,4-dinitrotoluene were recovered, representing 98.11% recovery. The material other than the 2,4-dinitrotoluene was titrimetrically analyzed to be 47.33% $HNO_3$.

This experiment demonstrates the passage of NO through a solution of 2,4-dinitrotoluene in aqueous nitric acid to decompose a substantial portion of the starting nitric acid, with a high efficiency of NO consumption. In this case, 83% of the nitric acid was recovered with an NO efficiency of 77%.

EXAMPLE 3

Decomposition of $HNO_3$ by NO

This example demonstrates decomposition of a simulated nitric acid phase.

Ten grams of 70.98% $HNO_3$ were added to a reaction flask kept at 0° C., while NO and $N_2$ were bubbled beneath the liquid level of the stirred acid. The flow rates throughout the reaction were approximately 10 sccm for $N_2$ and approximately 10 sccm for NO. The total reaction time was 126 minutes, with a total of 56.3 mmoles of NO passed through the solution, thus the resultant acid was determined to be 54.1% by weight.

EXAMPLE 4

NO Decomposition of 100% Nitric Acid

Into a reaction flask kept at room temperature was added 12.0 g of 100% nitric acid (190.8 mmole $HNO_3$). NO and $N_2$ were passed through the nitric acid solution at 50 sccm for $N_2$ and approximately 12 sccm for NO. The total reaction time was 177 minutes, after which remained 2.8 g of aqueous nitric acid of strength 52.6% by weight. Therefore, substantial decomposition of the concentrated nitric acid was effected, thus showing effectiveness for nitric acid recovery in a DNT system.

The product solution contained 23.7 mmole of $HNO_3$ and 74.7 mmole $H_2O$, the amount of $HNO_3$ being decomposed $= 190.8 - 23.7 = 167.1$ mmole. The NO passed was 95.4 mmole. Thus assuming the stoichiometry, $2HNO_3 + NO = 3NO_2 + H_2O$, we find in our reaction a $HNO_3/H_2O$ ratio of 2.2 and an efficiency of NO consumption of 78.3%. The total loss of mass over the reaction period was 9.18 g.

EXAMPLE 5

Continuous Countercurrent Nitric Acid Decomposition with Nitric Oxide 90 wt % nitric acid was admitted to the top of a 20-stage Oldershaw column at a rate of 29.6 g/min (0.423 moles/min $HNO_3$). Simultaneously, 8.04 g/min (0.268 moles/min) of nitric oxide was admitted to the reservoir at the bottom of the column. The column was operated at 44° C. and the contents of the reservoir were maintained at 81° C. by circulating warm water through the reservoir jacket. The flow of liquid into the reservoir was measured to be 12.3 g/min and was analyzed to be 50.72 wt % nitric acid, thus indicating that 76.6% of the nitric acid underwent decomposition to nitrogen dioxide and water. The flow of liquid overhead through the condenser was measured to be 25.5 g/min (92% of theoretical) and was a 5:1 mixture of nitrogen dioxide:nitric oxide.

What is claimed is:

1. In a process for extracting a dinitroaromatic compound selected from the group consisting of dinitrobenzene, dinitrotoluene and dinitroxylene from a reaction mixture comprising said dinitroaromatic composition, water, and nitric acid, said reaction mixture formed by reacting said dinitroaromatic composition using nitric acid only as the nitrating medium, which comprises the steps of:
  forming an organic layer containing said dinitroaromatic composition and an aqueous layer containing water and nitric acid; and
  decanting said dinitroaromatic composition from said aqueous layer, the improvement for enhancing the extraction of said dinitroaromatic composition from said aqueous layer which comprises the step of:
  contacting the aqueous layer with a sufficient amount of nitric oxide under conditions for reacting with substantially all of said nitric acid for forming gaseous nitrogen dioxide and liquid water, said nitric oxide being present in an amount sufficient to react with a substantial amount of said nitric acid and thereby forcing said dinitroaromatic composition into said organic layer because of insolubility in said aqueous layer; and then,
  separating the organic layer from the aqueous layer.

2. The process of claim 1 wherein said nitroaromatic compound is nitrotoluene.

3. The process of claim 2 wherein said nitrotoluene is dinitrotoluene.

4. The process of claim 1 wherein said nitroaromatic compound is nitrobenzene.

5. The process of claim 4 wherein said nitrobenzene is dinitrobenzene.

6. The process of claim 1 wherein said nitric oxide is added in an amount greater than 1 mole nitric oxide per 2 moles nitric acid.

7. the process of claim 6 wherein the nitric oxide is added under conditions such that reaction temperature is from 0° to 90° C.

8. A process for extracting a dinitroaromatic compound dissolved in a nitration medium containing water, nitric acid and dinitroaromatic compound which comprises
  (a) contacting the nitration medium with nitric oxide under conditions suited for reacting with nitric acid to form gaseous nitrogen dioxide and water and thereby form a medium of concentrated dinitroaromatic compound;
  cooling said medium to solidify said dinitroaromatic; and,
  separating said solidified nitroaromatic from said cooled nitration medium.

* * * * *